United States Patent
Whitworth et al.

(10) Patent No.: US 9,930,728 B2
(45) Date of Patent: Mar. 27, 2018

(54) VACUUM ASSISTED CONFORMAL SHAPE SETTING DEVICE

(75) Inventors: Denver R. Whitworth, North Richland Hills, TX (US); Vance N. Cribb, Aledo, TX (US); Eric W. Nottorf, Fort Worth, TX (US)

(73) Assignee: Textron Innovations Inc., Providence, RI (US)

(*) Notice: Subject to any disclaimer, the term of this patent is extended or adjusted under 35 U.S.C. 154(b) by 580 days.

(21) Appl. No.: 13/695,762

(22) PCT Filed: Jan. 3, 2011

(86) PCT No.: PCT/US2011/020016
§ 371 (c)(1),
(2), (4) Date: Nov. 1, 2012

(87) PCT Pub. No.: WO2012/093992
PCT Pub. Date: Jul. 12, 2012

(65) Prior Publication Data
US 2013/0043232 A1 Feb. 21, 2013

(51) Int. Cl.
*H05B 3/34* (2006.01)
*A61F 5/058* (2006.01)

(52) U.S. Cl.
CPC ............ *H05B 3/34* (2013.01); *A61F 5/05833* (2013.01); *H05B 2203/003* (2013.01); *H05B 2203/014* (2013.01); *H05B 2203/017* (2013.01)

(58) Field of Classification Search
CPC .... A61F 7/007; A61F 7/00; A61F 2007/0001; H05B 2203/014

USPC ........ 219/211, 209, 549, 528; 607/104, 108, 607/96, 114, 111

See application file for complete search history.

(56) References Cited

U.S. PATENT DOCUMENTS

| | | | | |
|---|---|---|---|---|
| 721,270 | A | * | 2/1903 | Zeckendorf .................... 219/549 |
| 1,358,509 | A | * | 11/1920 | Birkenfeld ..................... 219/211 |
| 1,399,095 | A | * | 12/1921 | Webb, Sr. ........................... 24/1 |
| 2,414,125 | A | | 1/1947 | Rheinfrank |
| 2,515,298 | A | * | 7/1950 | Feldman ........................ 126/204 |
| 2,842,771 | A | * | 7/1958 | Foti .................. A41D 19/01529 2/159 |

(Continued)

FOREIGN PATENT DOCUMENTS

| | | |
|---|---|---|
| DE | 10228015 | 1/2004 |
| EP | 0267640 | 10/1987 |

(Continued)

OTHER PUBLICATIONS

Canadian Office Action dated Jan. 22, 2015 from counterpart CA App. No. 2,824,582.

(Continued)

*Primary Examiner* — Dana Ross
*Assistant Examiner* — Lawrence Samuels
(74) *Attorney, Agent, or Firm* — James E. Walton

(57) ABSTRACT

A device and method for applying treatment to a structure includes a housing having a first membrane sealed to a second membrane for creating an airtight cavity therebetween for receiving a porous material and a working layer. The method includes the process of conforming the shape of the housing to the structure and applying a treatment thereafter to the structure.

18 Claims, 4 Drawing Sheets

(56) References Cited

U.S. PATENT DOCUMENTS

| | | | | |
|---|---|---|---|---|
| 3,867,939 A * | 2/1975 | Moore | A61F 7/02 | 604/291 |
| 4,098,279 A * | 7/1978 | Golden | A61F 7/02 | 607/104 |
| 4,149,529 A * | 4/1979 | Copeland et al. | 601/17 | |
| 4,206,751 A * | 6/1980 | Schneider | A61H 9/0078 | 601/152 |
| 4,250,397 A * | 2/1981 | Gray | H05B 3/36 | 219/212 |
| 4,370,975 A * | 2/1983 | Wright | A61H 9/0078 | 601/152 |
| 4,713,531 A * | 12/1987 | Fennekels et al. | 219/545 | |
| 4,935,971 A * | 6/1990 | Dunn | A61G 7/0005 | 4/516 |
| 5,074,285 A * | 12/1991 | Wright | A61H 9/0078 | 601/15 |
| 5,160,828 A * | 11/1992 | Olsen | 219/211 | |
| 5,302,806 A * | 4/1994 | Simmons | A41D 13/0051 | 219/211 |
| 5,417,720 A * | 5/1995 | Mason | A61F 5/05816 | 607/104 |
| 5,507,792 A * | 4/1996 | Mason | A61F 5/05816 | 601/15 |
| 5,620,621 A * | 4/1997 | Sontag | 219/211 | |
| 5,683,438 A * | 11/1997 | Grahn | 607/104 | |
| 6,565,593 B2 * | 5/2003 | Diana | 607/108 | |
| 6,974,428 B2 * | 12/2005 | Knutson et al. | 602/2 | |
| 6,987,209 B2 | 1/2006 | Augustine et al. | | |
| 7,224,256 B2 * | 5/2007 | Parsons | 338/25 | |
| 7,666,213 B2 * | 2/2010 | Freedman et al. | 607/104 | |
| 8,182,520 B2 * | 5/2012 | Schock | A61F 7/00 | 607/104 |
| 2003/0024684 A1 * | 2/2003 | Lyons et al. | 165/45 | |
| 2003/0040783 A1 * | 2/2003 | Salmon | 607/111 | |
| 2003/0109910 A1 * | 6/2003 | Lachenbruch et al. | 607/108 | |
| 2003/0191437 A1 * | 10/2003 | Knighton et al. | 604/133 | |
| 2004/0197521 A1 * | 10/2004 | Morriston | B32B 5/02 | 428/95 |
| 2004/0225341 A1 * | 11/2004 | Schock | A61F 7/00 | 607/104 |
| 2004/0244090 A1 * | 12/2004 | Langer | A41D 19/002 | 2/160 |
| 2005/0021114 A1 * | 1/2005 | Hidaka | A47C 7/748 | 607/112 |
| 2005/0027218 A1 * | 2/2005 | Filtvedt et al. | 601/152 | |
| 2005/0096714 A1 * | 5/2005 | Freedman et al. | 607/104 | |
| 2005/0172950 A1 * | 8/2005 | Aisenbrey | 126/208 | |
| 2005/0203452 A1 * | 9/2005 | Weston | A61M 1/0088 | 602/13 |
| 2005/0222526 A1 * | 10/2005 | Perry | A61H 9/0078 | 601/152 |
| 2005/0256556 A1 * | 11/2005 | Schirrmacher | A61F 7/02 | 607/104 |
| 2006/0276863 A1 * | 12/2006 | Kumamoto | A61F 7/034 | 607/96 |
| 2007/0068651 A1 * | 3/2007 | Gammons et al. | 165/46 | |
| 2007/0162096 A1 * | 7/2007 | Zakuto | A61F 7/02 | 607/104 |
| 2008/0000892 A1 * | 1/2008 | Hirano | B01L 3/50851 | 219/433 |
| 2008/0021531 A1 * | 1/2008 | Kane et al. | 607/111 | |
| 2008/0040831 A1 * | 2/2008 | Nilforushan et al. | 2/69 | |
| 2008/0132816 A1 * | 6/2008 | Kane | A61H 7/001 | 601/152 |
| 2008/0132976 A1 * | 6/2008 | Kane et al. | 607/104 | |
| 2008/0228245 A1 * | 9/2008 | Schock | A61F 7/00 | 607/104 |
| 2009/0114633 A1 * | 5/2009 | Naylor | H05B 1/0236 | 219/213 |
| 2009/0177184 A1 * | 7/2009 | Christensen et al. | 604/506 | |
| 2009/0312675 A1 * | 12/2009 | Sampson et al. | 601/10 | |
| 2010/0106230 A1 * | 4/2010 | Buchanan | A61F 7/00 | 607/111 |
| 2010/0137953 A1 * | 6/2010 | Stein | A41D 31/00 | 607/112 |
| 2010/0210982 A1 * | 8/2010 | Balachandran | A61F 7/0085 | 601/152 |
| 2011/0172749 A1 * | 7/2011 | Christensen et al. | 607/104 | |
| 2011/0238143 A1 * | 9/2011 | Schock | A61F 7/0053 | 607/104 |
| 2012/0191164 A1 * | 7/2012 | Gander | H05B 3/12 | 607/96 |
| 2013/0019374 A1 * | 1/2013 | Schwartz | 2/69 | |

FOREIGN PATENT DOCUMENTS

| | | |
|---|---|---|
| EP | 1319377 | 6/2003 |
| GB | 1438184 A | 6/1976 |
| WO | 0202181 | 1/2002 |

OTHER PUBLICATIONS

Canadian Office Action dated Jul. 24, 2015 from counterpart CA App. No. 2,824,582.

International Search Report and the Written Opinion of the International Searching Authority mailed by ISA/USA, U.S. Patent and Trademark Office dated Mar. 11, 2011 for International Patent Application No. PCT/US2011/020016, 7 pages.

European Search Report dated Nov. 27, 2012 from counterpart EP App. No. 11854920.3.

* cited by examiner

VACUUM ASSISTED CONFORMAL SHAPE SETTING DEVICE

TECHNICAL FIELD

The present invention relates generally to a surface conforming device utilizing vacuum to set a shape to a desired geometry to allow thermal devices to contact a surface, and more particularly, to a heating device adapted to retain a conformal shape of a structure.

DESCRIPTION OF THE PRIOR ART

Heating devices are well known in the art and are utilized for providing heat to a structure via a heat source. Conventional heat sources include electric coils, conduits for channeling hot fluids, chemicals, and so forth. In one embodiment, one or more electric wires could be disposed within a material, i.e., a heating blanket, for creating a heat source to warm a body. Another example is a hand warmer, which uses chemicals disposed within a material for providing heat to a person's hands.

Conventional heating devices have been shown to be effective in providing heat; however, in most cases, the heating devices are not adapted to conform and remain conformed to the working surface while providing heat thereto. An attachment device, i.e., an complex holding fixtures, can be utilized when attaching the heating device to the working surface; however, time and costs are expended when attaching the heating device to the structure.

Although the foregoing developments represent great strides in the area of heating devices, many shortcomings remain.

BRIEF DESCRIPTION OF THE DRAWINGS

The novel features believed characteristic of the application are set forth in the appended claims. However, the application itself, as well as a preferred mode of use, and further objectives and advantages thereof, will best be understood with reference to the following detailed description when read in conjunction with the accompanying drawings, wherein:

Figure 1:
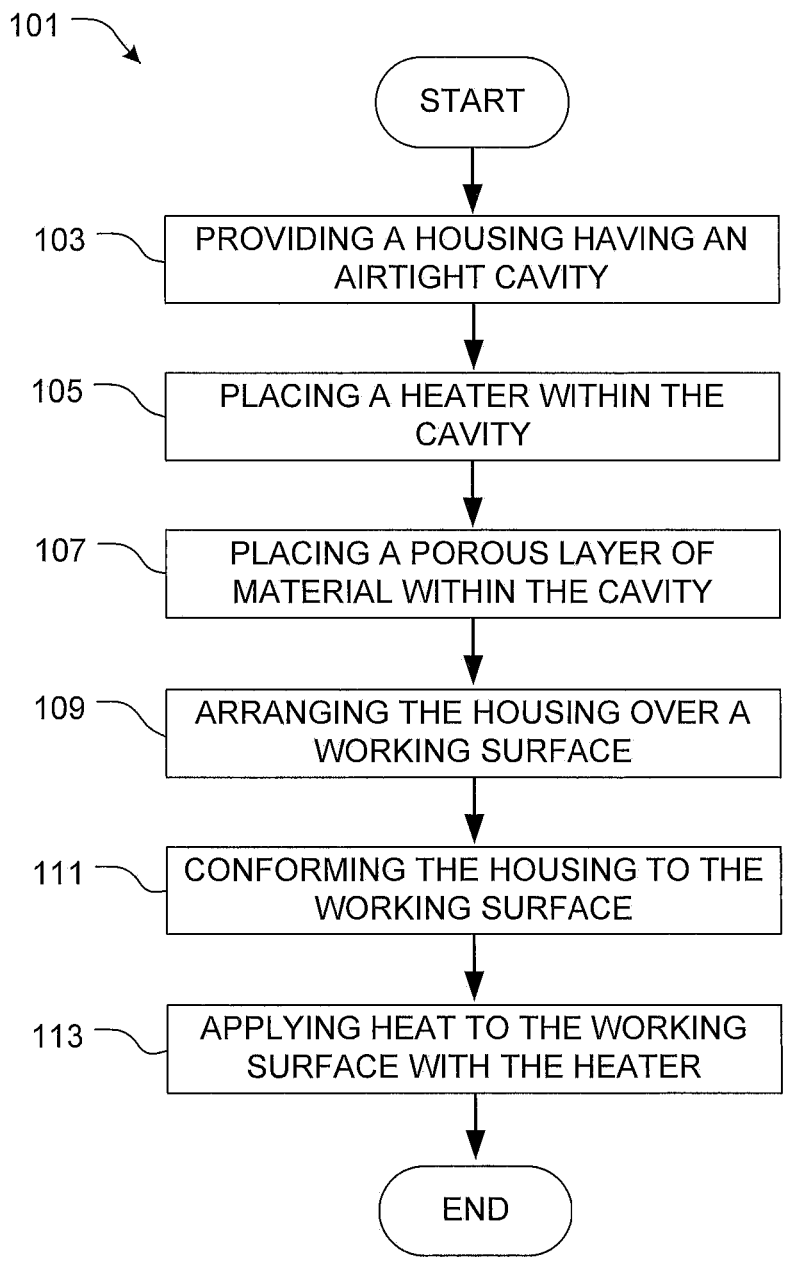
FIG. 1 is a flow chart depicting a method according to the preferred embodiment of the present application.

While the heating device of the present application is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as described herein.

DESCRIPTION OF THE PREFERRED EMBODIMENT

The heating device of the present application overcomes common disadvantages associated with conventional heating devices. Specifically, the heating device includes a housing having an airtight cavity and a conforming layer disposed therein, wherein the conforming layer is adapted to conform to the surfaces of the structure as air evacuated from the cavity, and includes a heater disposed within the cavity for applying heat to structure while the heating device remains conformed to the surfaces of the structure. The heating device allows rapid attachment and detachment from the structure without the need for an attachment device, for example, adhesive tape.

The heating device of the present application will be understood, both as to its structure and operation, from the accompanying drawings, taken in conjunction with the accompanying description. Several embodiments of the heating device are presented herein. It should be understood that various components, parts, and features of the different embodiments may be combined together and/or interchanged with one another, all of which are within the scope of the present application, even though not all variations and particular embodiments may be specifically illustrated in each figure.

Referring now to FIG. 1 in the drawings, a flow chart 101 shows a method for heating a structure according to the preferred embodiment of the present application. The preferred method includes a heating device adapted to conform and remain attached to the contoured surfaces of the structure while applying heat thereto. However, it should be appreciated that the preferred method could easily be adapted to provide other forms of treatment to the structure. For example, an alternative method could include the process of applying cooling, electrical, magnetic, and other forms of treatment to the structure.

In the preferred embodiment, the heating device is utilized with debulking and curing laminates having various geometric shapes. It should be appreciated that the preferred method can include the process of conforming the heating device directly to the contoured surface of the structure while the structure remains attached to a vehicle, thus allowing the process to be performed in-situ. It should be appreciated that the preferred method could easily be adapted for use in other fields such as in the filed of medicine where the heating device provides heat to a patient's leg.

The first step of the preferred method is represented in block 103, which includes assembling the heating device adapted to conform to the surfaces of the structure and apply heat thereto. The heating device includes a housing that forms an airtight inner cavity for receiving the various components of the heating device. A heater and porous material are placed within the cavity, as represented in block 105 and block 107, respectively, and the housing is thereafter sealed. After the heating device is manufactured, the worker places the heating device over the surface of the structure, as represented in block 109. The air within the housing is then evacuated with an external vacuum assembly, as represented in block 111. The evacuation process conforms the heating device to the surfaces of the structure and the fibers within the conforming layer are adapted to interlock with each other, thereby retaining the conformed shape. Finally, the heater is activated, thus providing heat to the structure, as represented in block 113. An alternative method includes measuring the temperature applied to the structure with a thermometer disposed within the cavity. The thermometer allows the worker to adjust the temperature of the heat applied to the structure.

Figure 2:
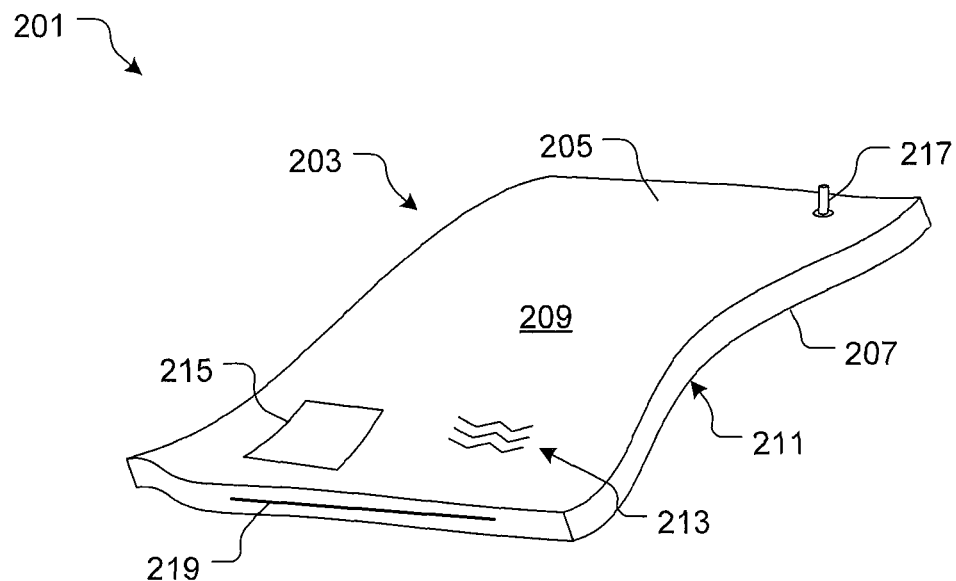
FIG. 2 is an oblique view of the heating device according to the preferred embodiment of the present application.
Figure 3:
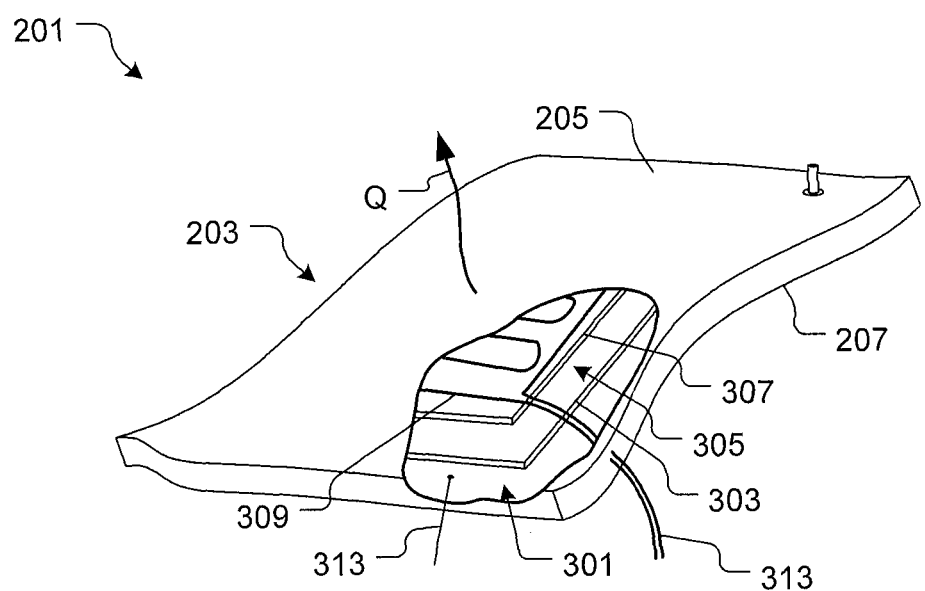
FIG. 3 is a an oblique view of the heating device of FIG. 2, the heating device being shown with a partially cutout view to show the components disposed therein.

FIGS. 2 and 3 show oblique views of a heating device 201 according to the preferred embodiment of the present application. FIG. 2 shows the surfaces of heating device 201, while FIG. 3 shows a partially cutout view of heating device 201, which illustrates the various components disposed therein.

Heating device 201 comprises a housing 203 having a first membrane 205 in sealing contact with a second membrane 207. Membrane 205 and membrane 207 form an airtight inner cavity therebetween for receiving one or more components of heating device 201. In the preferred embodiment, membrane 205 and membrane 207 are composed of an elastomeric material sufficiently durable for withstanding high negative vacuum pressures and for resisting puncturing when applied to sharp surface areas. It should be appreciated that the elastomeric material could be composed of a transparent material for viewing access into the inner cavity.

Membrane 205 includes a surface 209, and likewise membrane 207 includes a surface 211, both surfaces preferably including a smooth contouring. However, it should be appreciated that surface 209 and/or surface 211 could include a surface treatment 213, i.e., dimples and grooves, applied thereto for providing additional friction between housing 203 and the surfaces of the structure. Housing 203 could also include an attachment device 215 on surface 205 and/or surface 207 for securely fastening housing 203 to the structure. For example, attachment device 215 could include a clip, clamp, hook, magnet, quick-release device, and/or other suitable attachment devices.

Heating device 201 is further provided with a valve 217 in gaseous communication with the inner cavity of housing 203. Valve 217 is adapted to couple with a vacuum assembly (not shown) via a hose or other suitable conduit. During operation, the worker attaches a quick-release device to valve 217, which in turn opens valve 217 for gas passage therethrough. Thereafter, the worker activates the vacuum assembly to evacuate the air disposed with the inner cavity of housing 203.

Housing 203 can also include an opening 219 extending through the thickness of membrane 205 and adapted for allowing access into the inner cavity. During setup, the worker can utilize opening 219 for adding, removing or performing maintenance on the components disposed therein. It should be noted that when closed, opening 219 creates an airtight seal such that external air cannot enter within the inner cavity.

Referring now to FIG. 3 in the drawings, an oblique view of heating device 201 is shown. FIG. 3 shows membrane 205 and membrane 207 forming an airtight inner cavity 301 therebetween for receiving a porous material 303 and a heater 305.

Porous material 303 is preferable composed of a fiber mat having a random orientation of fiber disposed therein and is sufficiently sized to cover the majority of the inner surface area of cavity 301. Porous material 303 is adapted to conform to the surfaces of the structure and to retain the conformed position while heat is applied to the structure. In the preferred embodiment, porous material 303 is composed of material having random oriented fibers adapted to interlock under pressure, thus resulting in the fibers locking and retaining the conformed position. Porous material 303 is preferably composed of a cotton and/or polyester material having a thickness of about ¼ inch to about ½ inch. Of course, it should be understood that alternative embodiments could include different porous materials having the same or different thicknesses in lieu of the preferred embodiment.

Heater 305 preferably includes a heat absorbing layer of material 307 and one or more electric coils 309 disposed therein for providing heat "Q" to the structure. A wire 311 extends through housing 203 for coupling coils 309 and to an external power source. Heating device 201 is further provided with a thermocouple 313 for measuring and relaying the heat temperature applied by heater 305. In the preferred embodiment, thermocouple 313 extends through the thickness of membrane 205; however, thermocouple 313 could be attached to any surface of housing 201 in alternative embodiments. During operation, the worker inspects the heat temperature applied and adjusts the amount of electrical energy to coils 309, resulting in a desired heat temperature applied to the structure.

Figure 4:
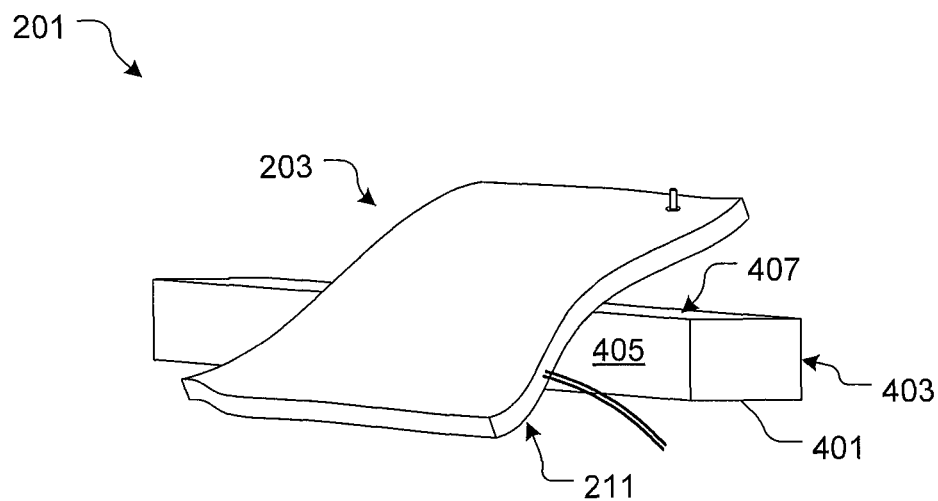
FIG. 4 is an oblique view of the heating device of FIG. 2 shown with a structure.

Referring now to FIG. 4 in the drawings, an oblique view of heating device 201 is shown with a structure 401. Structure 401 includes a surface 403, a surface 405, and a surface 407 that come into contact with surface 211 of housing 203. FIG. 4 shows heat device 201 operably associated with a structure having a rectangular shape; however, it should be appreciated that heat device 201 can be operably associated with structures having different geometric shapes. For example, heating device 201 could easily be utilized on a wing member or fuselage of an aircraft.

Figure 5:
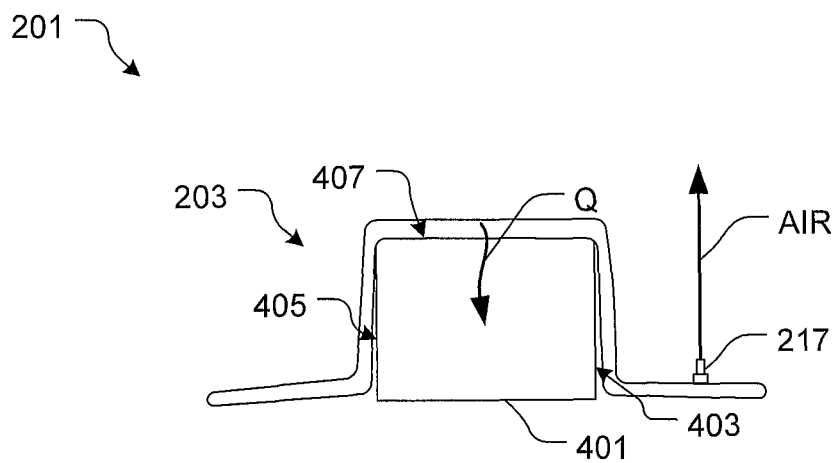
FIG. 5 is a front view of the structure and heating device of FIG. 4.

FIG. 5 shows heating device 201 conforming to the surfaces of structure 401. During operation, the worker places housing 203 against the surfaces of structure 401, then evacuates the air trapped within inner cavity 301 with a vacuum assembly coupled to valve 217, which in turn results in surface 211 of housing conforming to the surfaces of structure 401. Thereafter, heater 305 provides heat "Q" to structure 301 upon activation of the external power source.

Figure 6:
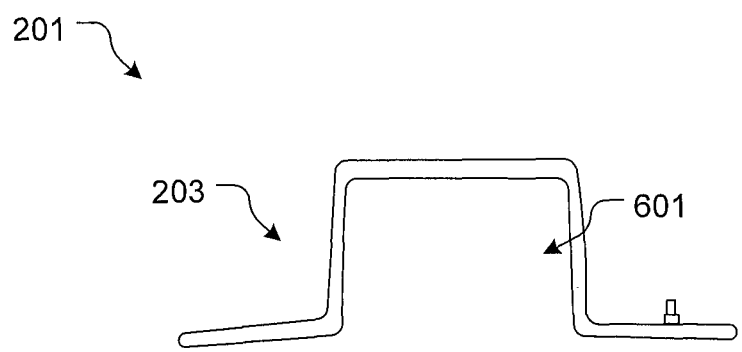
FIG. 6 is a front view of the heating device of FIG. 4.

Referring now to FIG. 6 in the drawings, an alternative application of heating device 201 is shown. It should be appreciated that heating device 201 could be used as a mold or similar means after being conformed in the desired shaped. FIG. 6 shows housing 203 having a conduit profile after conforming to the surfaces of structure 401. It should be appreciated that housing 203 could conform to other geometric shapes, thus, providing a matching mold to the general shape of the structure. Thereafter, the worker can utilize heating device 201 as a mold for manufacturing additional structures.

Figure 7:
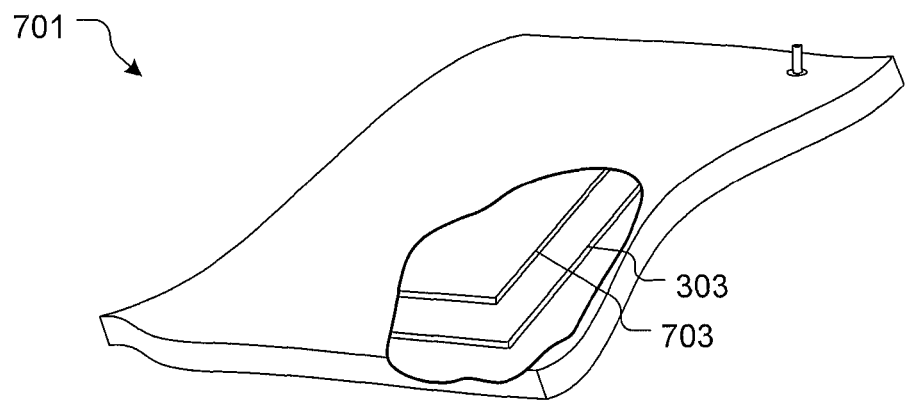
FIG. 7 is an oblique view of an alternative embodiment of the heating device of FIG. 2.

FIG. 7 is an oblique view of an alternative embodiment of heating device 201. Heating device 701 is substantially similar in form and function to heating device 201. It should be understood heating device 701 can include the features of heating device 201, and likewise, heating device 201 can include the features of heating device 701. Heating device 701 comprises of a porous material 703 substantially similar in form and function to porous material 303. Heating device 701 further comprises a working layer 705 utilized for providing a treatment to a structure, i.e., cooling, electricity, magnetism, and other forms of treatment. In one embodiment, layer 705 is a cooler having one or more conduits disposed therein for channeling a cool fluid, thus applying cooling to the structure.

Figure 8:
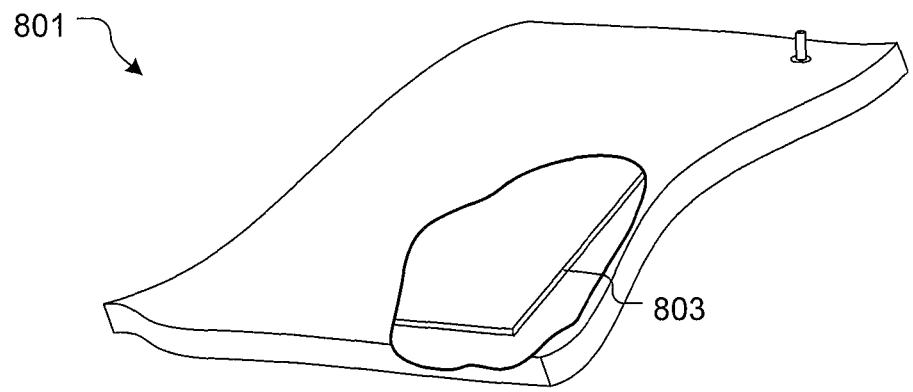
FIG. 8 is an oblique view of an alternative embodiment of the heating device of FIG. 2.

FIG. 8 is an oblique view of an alternative embodiment of heating device 201. Heating device 801 is substantially similar in form and function to heating device 201. It should be understood heating device 801 can include the features of heating device 201, and likewise, heating device 201 can include the features of heating device 801. Heating device 801 comprises of a porous material 803 substantially similar porous material 303, however, porous material 803 also includes the features of layer 705 and/or heater 305. For example, in lieu of having two components, i.e., a porous material and a heater, device 801 comprises a single porous material 803 adapted to conform to the surfaces of the structure and to provide heat, cooling, electricity, magnetism, and/or other forms of treatment to the structure.

It is evident by the foregoing description that the heating device has significant benefits and advantages over conventional heating devices. In particular, the heating device conforms to a working surface and retained the conformed shape while applying heat. In addition, the heating device can be adapted to provide other forms of treatment, i.e., cooling, to the structure. The heating device can be adapted for use in various fields such as composites on an aircraft fuselage and/or applied in the medical filed such as applying heat to an injured leg.

The particular embodiments disclosed above are illustrative only, as the invention may be modified and practiced in different but equivalent manners apparent to those skilled in the art having the benefit of the teachings herein. It is therefore evident that the particular embodiments disclosed above may be altered or modified, and all such variations are considered within the scope and spirit of the invention. Accordingly, the protection sought herein is as set forth in the description. It is apparent that an invention with significant advantages has been described and illustrated, Although the present invention is shown in a limited number of forms, it is not limited to just these forms, but is amenable to various changes and modifications without departing from the spirit thereof.

The invention claimed is:

1. A device for providing treatment to a surface of a structure, the device comprising:
    a housing having:
        a first membrane sealed to a second membrane, the first membrane and the second membrane forming an airtight cavity therebetween;
    a polyester mat having thickness of between ¼ inch to ½ inch and disposed within the cavity, the polyester mat having material composed of a plurality of random oriented fibers configured to interlock under pressure and configured to conform to the surface of the structure, the plurality of random oriented fibers being configured to retain the conformed shape of the surface of the structure after the air is evacuated from the airtight cavity;
    a working layer disposed within the cavity, the working layer being adapted to apply treatment to the structure; and
    a valve attached to the housing and extending through the first membrane, the valve being configured to provide channeling access to the air disposed within the airtight cavity;
    wherein the first membrane and the second membrane are grooved externally to the airtight cavity and are configured to provide additional friction between an internal surface of the housing and the surface of the structure;
    wherein the housing is rigid enough to act as a mold after the air is evacuated from the airtight cavity;
    wherein during use, the housing conforms to the contoured shape of the structure as air is evacuated, the material disposed therein retains the contoured shape, and the working layer applies treatment to the structure; and
    wherein the plurality of random oriented fibers are configured to interlock with each other as pressure is applied thereto.

2. The device of claim 1, wherein the first membrane and the second membrane are composed of an elastomeric material.

3. The device of claim 1, wherein the working layer is a heater.

4. The device of claim 3, the heater comprising:
    a heat absorbing material; and
    an electrical coil disposed within the heat absorbing material;
    wherein electricity is passed through the electrical coil, thereby providing heat to the structure.

5. The device of claim 3, further comprising:
    a thermocouple disposed within the cavity, the thermocouple being adapted to measure the temperature of the of the heat applied by the heater.

6. The device of claim 1, wherein the working layer is a cooler adapted to chill the structure.

7. A device for applying heat to a surface of a structure, the device comprising:
    a housing having:
        a first membrane sealed to a second membrane, the first membrane and the second membrane forming an airtight cavity therebetween;
    a polyester mat having thickness of between ¼ inch to ½ inch and disposed within the cavity, the mat having material composed of a plurality of random oriented fibers configured to interlock under pressure and configured to conform to the surface of the structure, the plurality of random oriented fibers being configured to retain the conformed shape of the surface of the structure after the air is evacuated from the airtight cavity;
    a heater disposed within the cavity, the heater being adapted to apply heat to the structure; and
    a valve attached to the housing and extending through the first membrane, the valve being configured to provide channeling access to the air disposed within the airtight cavity;
    wherein the first membrane and the second membrane are externally grooved, dimpled, and are configured to provide additional friction between an internal surface of the housing and the surface of the structure;
    wherein the housing is rigid enough to act as a mold after the air is evacuated from the airtight cavity;
    wherein during use, the housing conforms to the contoured shape of the structure as air is evacuated, the material disposed therein retains the contoured shape, and the heater applies heat to the structure; and
    wherein the plurality of random oriented fibers are configured to interlock with each other as pressure is applied thereto.

8. The device of claim 7, wherein the first membrane and the second membrane are composed of an elastomeric material.

9. The device of claim 7, the heater comprising:
    a heat absorbing material; and
    an electrical coil disposed within the heat absorbing material;
    wherein electricity is passed through the electrical coil, thereby providing heat to the structure.

10. The device of claim 7, further comprising:
a thermocouple disposed within the cavity, the thermocouple being adapted to measure the temperature of the of the heat applied by the heater.

11. A method for providing treatment to a surface of a structure, the method comprising:
providing a housing having an airtight cavity;
placing a polyester mat having thickness of between ¼ inch to ½ inch within the cavity, the polyester mat having material composed of a plurality of random oriented fibers configured to interlock under pressure and configured to conform to the surface of the structure, the plurality of random oriented fibers being configured to retain the conformed shape of the surface of the structure after the air is evacuated from the airtight cavity;
grooving an external surface of the housing to increase friction between an internal surface of the housing and the surface of the structure;
placing a working layer within the cavity;
positioning the device over the surface of the structure;
interlocking the plurality of random oriented fibers by evacuating air trapped within the airtight cavity; and
applying treatment to the structure by activating the working layer;
wherein the housing is sufficiently rigid to act as a mold after the air is evacuated from the airtight cavity.

12. The method of claim 11, wherein the process of applying treatment includes applying heat to the structure with a heater.

13. The method of claim 12, further comprising:
providing a heat absorbing material having coils disposed therein; and
producing heat by passing an electric current through the coil.

14. The method of claim 12, further comprising:
monitoring the temperature of heat treatment with a thermocouple disposed within the cavity;
adjusting the amount of electric current to achieve a desire temperature.

15. The method of claim 11, wherein the process of applying treatment includes chilling the structure with a cooler.

16. The method of claim 11, further comprising:
providing an opening in the housing;
wherein the opening allows access to the structure during setup.

17. The device of claim 7, further comprising:
an opening in the housing;
wherein the opening is airtight when closed.

18. The device of claim 1, further comprising:
an opening in the housing;
wherein the opening is airtight when closed; and
wherein the opening allows access to the surface of the structure when opened during setup.

* * * * *